United States Patent [19]

Gilman et al.

[11] Patent Number: 5,607,833

[45] Date of Patent: Mar. 4, 1997

[54] CELL-FREE ASSAY FOR COMPOUNDS WHICH ACTIVATE OR BLOCK INACTIVATION OF CELL PROLIFERATION

[75] Inventors: Michael Z. Gilman, Huntington; Henry B. Sadowski, East Northport, both of N.Y.

[73] Assignee: Cold Spring Harbor Laboratory, Cold Spring Harbor, N.Y.

[21] Appl. No.: 420,339

[22] Filed: Apr. 11, 1995

Related U.S. Application Data

[63] Continuation of Ser. No. 960,889, Oct. 14, 1992, abandoned.

[51] Int. Cl.$^6$ .................................................. C12Q 1/68
[52] U.S. Cl. .............................. 435/6; 435/7.21; 436/503; 436/813
[58] Field of Search ................................ 435/6, 7.21, 7.4, 435/7.8; 436/503, 518

[56] References Cited

PUBLICATIONS

Wagner, B. J., et al., "The SIF binding element confers sis/PDGF inducibility onto the c–fos promoter," *EMBO* 9(13)4477–4484 (1990).

Ryan, W. A., et al., "Two distinct cellular phosphoproteins bind to the c–fos serum response element," *EMBO* 8(6)1785–1792 (1989).

Gilman, Michael Z., "The c–fos serum response element responds to protein kinase C–dependent and –independent signals but not to cyclic AMP," *Genes & Development* 2:394–402 (1988).

Greenberg, M. E., et al., "Stimulation of 3T3 cells induces transcription of the c–fos proto–oncogene," *Nature* 311:433–438 (1984).

Stumpo, D. J., et al., "Identification of c–fos Sequences Involved in Induction by Insulin and Phorbol Esters," *J. Biol. Chem.* 4:1611–1614 (1988).

Hayes, T. E., et al., "Inducible binding of a factor to the c–fos regulatory region," *Proc. Natl. Acad. Sci. USA* 84:1272–1276 (1987).

Stumpo, D. J., et al., "Insulin and growth factor effects on c–fos expression in normal and protein kinase C–deficient 3T3–L1 fibroblasts and adipocytes," *Proc. Natl. Acad. Sci. USA2* 83:9453–9457 (1986).

Cantley, L. C., et al., "Oncogenes and Signal Transduction," *Cell* 64:281–302 (1991).

Herrera, R. E., et al., "Occupation of the c–fos serum response element in vivo by a multi–protein complex is unaltered by growth factor induction," *Nature* 340:68–70 (1989).

Schindler, C., et al., "Interferon–Dependent Tyrosine Phosphorylation of a Latent Cytoplasmic Transcription Factor," *Science* 257:809–812 (1992).

David, M., et al., "Activation of Transcription Factors by Interferon–α in a Cell–Free System," *Science* 257:813–815 (1992).

Koch, A. C., et al., "SH2 and SH3 Domains: Elements That Control Interactions of Cytoplasmic Signaling Proteins," *Science* 252:668–673 (1991).

Williams, L. T., "Signal Transduction by the Platelet–Derived Growth Factor Receptor," *Science* 243:1564–1570 (1989).

Lee, K. A., et al., "A Small–Scale Procedure for Preparation of Nuclear Extracts that Support Efficient Transcription and Pre–mRNA Splicing," *Gene Anal. Tech.* 5:22–31 (1988).

*Primary Examiner*—Christine M. Nucker
*Assistant Examiner*—Donna C. Wortman
*Attorney, Agent, or Firm*—Hamilton, Brook, Smith & Reynolds, P.C.

[57] ABSTRACT

This invention pertains to a method of assessing the ability of a compound to block or activate cell proliferation by assessing its effect on a cellular signal transduction pathway whose activation results in cell proliferation. In the present method, a cell-free system is used to assess the ability of a compound to block or activate a signal transduction pathway which is activated by binding of a growth factor to a cell surface receptor with intrinsic tyrosine kinase activity and whose activation results in proliferation of the cells to which growth factor has bound. Cellular signal transduction involves multiple pathways, each consisting of one or more steps emanating from a specific protein bound to a single receptor which is specific for that protein and located on the cell surface or within the cell.

5 Claims, 1 Drawing Sheet

CELL-FREE ASSAY FOR COMPOUNDS WHICH ACTIVATE OR BLOCK INACTIVATION OF CELL PROLIFERATION

RELATED APPLICATIONS

This application is a continuation of application Ser. No. 07/960,889 filed on Oct. 14, 1992, now abandoned, which is incorporated herein by reference in its entirety.

BACKGROUND

Although the cellular signal transduction pathways involved in growth control of cells are not fully understood, it is known that there are at least four types of proteins that participate in the process: growth factors, receptors, intracellular signal transducers, and intranuclear transcriptional controllers. Growth factors are one way a cell sends a message to another cell. The cell responding to the growth factor has a specific receptor that is sensitive to the growth factor. Since different cells have different receptors, each signal can produce a response in some cell types but not in others. Occupancy of growth factor is sensed by the cell and if metabolic conditions are favorable, the cell completes the growth cycle and gives rise to two cells similar to the original.

The chain of events that leads to cell growth is initiated by growth factor-receptor interactions which produce a signal in the cell. The cell interprets the signal and often stimulates intracellular signal transducers, or secondary messengers, that alter transcription, either by expressing new genes or modifying levels of expression of presently active genes. Not all second messenger activity is focused on transcription. Changes in cell shape and metabolism, for example, can be induced by the action of signals directly on existing cellular proteins.

The transcriptional response to a growth signal alters the protein composition of the cell providing the critical proteins needed for cell growth. Transcription is controlled by two types of DNA sequences: promoters, located at the start of transcription, and enhancers, located farther from the start site and able to act over long distances. Both types of sequences function through specific intranuclear transcriptional controllers or binding proteins that recognize short sequence motifs within the promoters and enhancers. These bound factors then accelerate or retard the initiation of transcription of proteins for cell growth.

Control of cell growth is an important aspect of an animal's physiology. Cells of an adult must divide frequently enough to allow tissues to remain in a steady state and division must be stimulated in instances where an immune response is required or where cell division must be stimulated, for example, at the site of a wound. Uninhibited growth of cells may result in tumor formation, and therefore control of cell growth is an area of considerable interest, particularly as it relates to cancer research. Therefore, it would be beneficial to understand cellular signal transduction pathways because of the potential for treating proliferative disorders.

SUMMARY OF THE INVENTION

This invention pertains to a method of assessing the ability of a compound to inhibit activation of or activate cell proliferation by assessing its effect on a cellular signal transduction pathway whose activation results in cell proliferation. In the present method, a cell-free system is used to assess the ability of a compound to activate or inhibit activation of a signal transduction pathway which is activated by binding of a growth factor to a cell surface receptor with intrinsic tyrosine kinase activity and whose activation results in proliferation of the cells to which growth factor has bound. Cellular signal transduction involves multiple pathways, each consisting of one or more steps emanating from a specific protein bound to a single receptor which is specific for that protein and located on the cell surface or within the cell. The method of the present invention measures one of these pathways which allows for screening for compounds that block any step of a cellular signal transduction pathway, where such a step may be specific to a particular pathway, or common to many pathways.

In the present method, binding of a DNA-binding protein with its DNA binding partner, which is an oligonucleotide sequence which specifically binds the DNA-binding protein, is detected. Binding of the DNA-binding protein with its DNA binding partner is activated in vivo by binding of a growth factor to a cell surface receptor which has intrinsic tyrosine kinase activity and whose activation results in activation of a cellular signal transduction pathway in cells to which the growth factor binds, causing proliferation of the cells. Thus, binding of the DNA-binding protein with its DNA binding partner is indicative of activation of tyrosine kinase activity of a cell surface receptor by binding of a growth factor and the resulting activation of a cellular signal transduction pathway associated with (whose activation results in) cell proliferation. Conversely, inhibition (complete or partial) of binding of the two pair members is indicative of inhibition (complete or partial) of activation of such a cellular pathway and, thus, inhibition of cell proliferation. The present method is useful to assess the ability of a compound (i.e., a compound being assessed) to activate or inhibit activation of a cellular signal transduction pathway. Binding or lack of binding of the DNA-binding protein with its DNA-binding partner is detected in the presence of the compound to be assessed and in the presence and absence of an agent which activates the tyrosine kinase activities of cell surface growth factor receptors present on cell plasma membranes. If binding of the DNA-binding protein with its DNA-binding partner does not occur or occurs to a lesser extent in the presence of the compound to be assessed when an agent such as growth factor is present, the compound is an inhibitor of the cellular signal transduction pathway. If binding of the DNA-binding protein and its DNA-binding partner occurs in the presence of the compound to be assessed and in the absence of an agent such as a growth factor, the compound is an activator of activation of the cellular signal transduction pathway. It is also possible using the method of the present invention to identify an enhancer of activation of the cellular signal transduction pathway. In this case, activation in the presence of the compound to be assessed and an agent such as growth factor occurs to a greater extent than in the presence of growth factor alone.

The present method is carried out in a cell-free system in which the combination of reagents is determined by whether the assay is used to identify an inhibitor or an activator of signal transduction pathways.

In the embodiment in which an inhibitor is to be identified, the following reagents are combined to produce a test sample: the compound to be assessed; a partially soluble membrane fraction from cells with cell surface growth factor receptors; a cytoplasmic fraction from any cells containing DNA-binding protein whose binding to its DNA-binding partner is activated by activation of the tyrosine kinase activities of the cell surface receptors present in the membrane fraction; an agent which activates the tyrosine kinase activities of cell surface growth factor receptors present on the membrane fraction; adenosine triphosphate (ATP); magnesium; manganese; and a DNA-binding partner of the DNA-binding protein (i.e., an oligonucleotide sequence which specifically binds the DNA-binding protein present in the cytoplasmic fraction). The agent which activates the tyrosine kinase activities of the cell surface growth factor receptors in the membrane fraction is a growth factor which binds to the growth factor receptors or a detergent present at a concentration sufficient to partially solubilize the membrane fraction and activate the tyrosine kinase activities of the growth factor receptors. In this case, the ability of the compound to inhibit the cellular signal transduction pathway in the presence of the agent which activates the tyrosine kinase activities of cell surface growth factor receptors present on the membrane fractions in the test sample is determined by comparing the results with those obtained using an appropriate control (i.e., the same reagents as in the test sample except no compound is present). If binding of the DNA-binding protein with its DNA-binding partner does not occur or occurs to a lesser extent in the presence of the compound to be assessed when an agent such as growth factor is present, the compound is an inhibitor of the cellular signal transduction pathway.

In the embodiment in which an activator of the cellular signal transduction pathway is to be identified, the following reagents are combined to produce a test sample: the compound to be assessed; a partially soluble membrane fraction from cells with cell surface growth factor receptors; a cytoplasmic fraction from any cells containing DNA-binding protein whose binding to its DNA-binding partner is activated by activation of the tyrosine kinase activities of the cell surface receptors present in the membrane fraction; adenosine triphosphate (ATP); magnesium; manganese; and a DNA-binding partner of the DNA-binding protein (i.e., an oligonucleotide sequence which specifically binds the DNA-binding protein present in the cytoplasmic fraction). In this case, the ability of the compound to activate the cellular signal transduction pathway in the absence of the agent which activates the tyrosine kinase activities of cell surface growth factor receptors present on the membrane fractions in the test sample is determined by comparing results with those obtained using a control (i.e., the same reagents as in the test sample except no compound is present). In this case, the compound to be assessed is an activator of a signal transduction pathway if it activates the tyrosine kinase activities of cell surface growth factor receptors present on the membrane fractions. If binding of the DNA-binding protein and its DNA-binding partner occurs in the presence of the compound to be assessed and in the absence of an agent such as a growth factor, the compound is an activator of activation of the cellular signal transduction pathway.

The amount of unbound DNA (i.e., the DNA binding partner) or bound DNA in the test sample is compared to the corresponding DNA (unbound or bound) in the control by any method which allows separation of free DNA from bound DNA and detection of the resulting separated DNA. If binding of the DNA-binding protein with its DNA-binding partner does not occur or occurs to a lesser extent in the presence of the compound to be assessed when an agent such as growth factor is present, the compound is an inhibitor of the cellular signal transduction pathway. If binding of the DNA-binding protein and its DNA-binding partner occurs in the presence of the compound to be assessed and in the absence of an agent such as a growth factor, the compound is an activator of activation of the cellular signal transduction pathway. It is also possible using the method of the present invention to identify an enhancer of activation of the cellular signal transduction pathway. In this case, activation in the presence of the compound to be assessed and an agent such as growth factor occurs to a greater extent than in the presence of growth factor alone.

The method of the present invention is useful for identifying compounds which may be useful in treating proliferative disorders, such as cancer, by reducing (totally or partially) cell growth associated with cancer, in enhancing the immune system by stimulating growth of immune response cells, and possibly in "jump-starting" cell growth in cells that normally do not grow or accelerating the growth of certain cells.

DETAILED DESCRIPTION OF THE INVENTION

The present invention is a method of identifying a compound which alters (inhibits activation of or activates) a cellular signal transduction pathway which is activated by binding of a growth factor to a cell surface receptor and which, upon activation, signals cells to proliferate. In particular, the present method is an assay for assessing the ability of a compound to block or activate a cellular signal transduction pathway which is activated by binding of a growth factor to a cell surface receptor which has intrinsic tyrosine kinase activity and which, once activated, signals cells in which it is activated to proliferate. Compounds which activate or inhibit activation of the cellular signal transduction pathway and, thus, inhibit or enhance cell proliferation, can be identified using the present method. Compounds identified by the present method can be used to alter cell proliferation (i.e., inhibit, partially or totally, or enhance proliferation) and have applications in any disease or condition where cell proliferation is abnormal. Compounds identified by the present method as inhibitors of a signal transduction pathway (and, thus, as inhibitors of cell proliferation) are useful, for example, in preventing or reducing the extent of abnormally rapid or extensive cell proliferation evident in tumor formation, leukemias and other forms of malignancy; or preventing normal cell growth, for example, in situations requiring immunosupression. Compounds identified by the present method as activators or enhancers of a signal transduction pathway (and, thus, as enhancers of cell proliferation) are useful, for example, in any instance in which cell proliferation is to be enhanced (i.e., made to occur to a greater extent and/or at a faster rate than occurs prior to or in the absence of the enhancer compound), such as to stimulate production/proliferation of immune system cells (e.g., to mobilize T-cells for tumor treatment or viral infections) and to "jump start" cells which normally do not proliferate (e.g., stimulating nerve cell growth, treating degenerative diseases, or facilitating wound healing).

In the method of the present invention, the ability of a compound to activate or block activation of a cellular signal transduction pathway (and, thus, to block or activate cell proliferation) is assessed by detecting binding of a DNA binding protein to its binding partner (an oligonucleotide which specifically binds the DNA binding protein). Binding of the DNA binding protein and its binding partner is activated by binding of a growth factor to a cell surface receptor which has tyrosine kinase activity and which, upon activation, stimulates a cellular signal transduction pathway which, in turn, signals cells to proliferate.

Many genes involved in cell growth are regulated by signaling molecules, such as a growth factor protein, that bind to specific receptor proteins on the surface of cells. A receptor protein on the surface of target cells, or in its nucleus or cytosol, has a binding site with a high affinity for a particular signaling molecule such as growth factor proteins. When the growth factor binds to the receptor, the receptor-growth factor complex initiates a sequence of reactions that changes the function of the cell.

The response of a cell or tissue to specific growth factors is dictated by the particular growth factor receptors it possesses and by the intracellular reactions initiated by the binding of any one growth factor to its receptor. A cell may have two or more types of receptors or different sets of receptors for the same growth factor. Alternatively, the same receptor may occur on various cell types, and binding of the same growth factor may trigger a different response in each type of cell.

In most receptor-growth factor systems, the growth factor's function appears to be binding to and activation of the cell surface receptors which are believed to undergo a conformational change upon binding by the growth factor at the cell exterior. The receptors are (or are closely associated with) protein kinases, which are enzymes that utilize adenosine triphosphate (ATP) to phosphorylate proteins and are activated by binding of a growth factor. Phosphorylated forms of many enzymes are much more active than unphosphorylated forms; the phosphorylated forms of other enzymes are less active. This change leads to generation of an intracellular signal that alters the behavior of that cell. The intracellular signaling molecule is also referred to as a secondary messenger, the first messenger being the growth factor.

A specific example of a receptor-growth factor system is stimulation of cell proliferation by binding of epidermal growth factor (EGF) to epidermal receptor proteins on the surface of epidermal cells and a variety of other cells. The EGF receptor is a single polypeptide chain that spans the plasma membrane. The extracellular side of the receptor contains the binding site for EGF. The cytosolic side of the EGF receptor contains a tyrosine kinase domain that becomes activated by the binding of EGF to transfer phosphate from ATP to tyrosine residues on specific cellular proteins, including the receptor protein itself and other plasma membrane and cytosolic proteins. Autophosphorylation of the receptor protein increases its capacity to phosphorylate tyrosine residues on target proteins.

The importance of tyrosine kinases in growth control is highlighted by the finding that tyrosine phosphorylation also plays a major role in the control mechanisms of oncogenes, which transform normal cells into a cancerous state. Most oncogenes are derivatives of certain normal cellular genes, called proto-oncogenes, which are important for normal cellular growth but can be altered, simply, to become oncogenes. This suggests that oncogenes interact with the growth controlling systems of cells. One such gene is the viral src gene which has the capacity to direct the synthesis of a sarcoma-producing protein that is bound to the cytosolic surface of the plasma membrane of a cell and phosphorylates tyrosine residues on proteins. While the control mechanisms underlying this transmembrane signaling in normal cells and abnormal cells, such as cancer cells, is still poorly understood, the cellular signal transduction involves multiple pathways emanating from a single receptor which can be modified to assess the ability of a compound to activate or inhibit cellular signal transduction pathways.

As described herein, growth factors such as epidermal growth factor (EGF) and platelet derived growth factor (PDGF) have been shown to bind to and activate cell surface receptors with intrinsic tyrosine kinase activities, eliciting multiple physiological changes in target cells, including alterations in gene expression. Receptor tyrosine kinase signaling involves recruitment of specific proteins into a signaling complex through interactions between receptor autophosphorylation sites and the src-homology region-2 (SH2) domains on these signaling proteins. Diverse signals can subsequently be generated, depending on the specific receptor and cell type. How such signals are transmitted to the nucleus remains poorly understood, but because the transcriptional activation of many genes by growth factor occurs in the absence of new protein synthesis, one or more signals emanating from growth factor receptors must directly affect transcription factors. Applicants describe herein the activation of a DNA-binding protein in a cell-free system where activation of a DNA-binding requires growth factor receptors, adenosine triphosphate (ATP), and phosphotyrosine-SH2 interactions.

In the method of the present invention, binding of a DNA-binding protein to its binding partner is detected as an indicator of activation of a cellular signal transduction pathway. The present method is carried out in a cell-free system in which the combination of reagents are determined by whether the assay is used to identify an inhibitor or an activator of signal transduction pathways.

In the embodiment in which an inhibitor is to be identified, the following reagents are combined to produce a test sample: the compound to be assessed; a partially soluble membrane fraction from cells with cell surface growth factor receptors; a cytoplasmic fraction from any cells containing DNA-binding protein whose binding to its DNA-binding partner is activated by activation of the tyrosine kinase activities of the cell surface receptors present in the membrane fraction; an agent which activates the tyrosine kinase activities of cell surface growth factor receptors present on the membrane fractions; adenosine triphosphate (ATP); magnesium; manganese; and a DNA-binding partner of the DNA-binding protein (i.e., an oligonucleotide sequence which specifically binds the DNA-binding protein present in the cytoplasmic fraction). The agent which activates the tyrosine kinase activities of the cell surface growth factor receptors in the membrane fraction is a growth factor which binds to the growth factor receptors or a detergent present at a concentration sufficient to partially solubilize the membrane fractions and activate the tyrosine kinase activities of the growth factor receptors. In this case, the ability of the compound to affect (inhibit the cellular signal transduction pathway in the presence of the agent which activates the tyrosine kinase activities of cell surface growth factor receptors present on the membrane fractions) activation in the test sample is determined by comparing the results with those obtained using an appropriate control (i.e., the same reagents as in the test sample except no compound is present). If binding of the DNA-binding protein with its DNA-binding partner does not occur or occurs to a lesser extent in the presence of the compound to be assessed when an agent such as growth factor is present, the compound is an inhibitor of the cellular signal transduction pathway.

In the embodiment in which an activator of the cellular signal transduction pathway is to be identified, the following reagents are combined to produce a test sample: the compound to be assessed; a partially soluble membrane fraction from cells with cell surface growth factor receptors; a cytoplasmic fraction from any cells containing DNA-binding protein whose binding to its DNA-binding partner is activated by activation of the tyrosine kinase activities of the cell surface receptors present in the membrane fraction; adenosine triphosphate (ATP); magnesium; manganese; and a DNA-binding partner of the DNA-binding protein (i.e., an oligonucleotide sequence which specifically binds the DNA-binding protein present in the cytoplasmic fraction). In this case, the ability of the compound to affect (activate the cellular signal transduction pathway in the absence of the agent which activates the tyrosine kinase activities of cell surface growth factor receptors present on the membrane fractions) activation in the test sample is determined by comparing results with those obtained using a control (i.e., the same reagents as in the test sample except no compound is present). In this case, the compound to be assessed is an activator of the signal transduction pathway if it activates the tyrosine kinase activities of cell surface growth factor receptors present on the membrane fractions. If binding of the DNA-binding protein and its DNA-binding partner occurs in the presence of the compound to be assessed and in the absence of the an agent such as a growth factor, the compound is an activator of activation of the cellular signal transduction pathway.

In both embodiments, the cell membrane fraction has at least one type of growth factor receptor and the cytoplasmic fraction used in the assay includes a DNA binding protein whose binding to its binding partner is activated by activation of the tyrosine kinase activities of the type of growth factor receptor whose participation in signal transducction is being assessed. In each embodiment, the resulting combination is maintained under appropriate conditions (e.g., temperature, pH, sufficient time) for the growth factor present in the combination to bind cell surface receptors in the cellular membrance fraction, the signal transduction pathway to be activated and the DNA binding protein to bind with its binding partner. The present method can be carried out at a variety of temperatures and will typically be carried out at a temperature from 0° C. to 37° C. and, preferably between 30° C. to 37° C. and even more preferably at 30° C. or 37° C. The method can be carried out as a series of steps or as a single (one-step) method. In the method of the present invention, the following reagents must be present: adenosine triphosphate (at a final concentration in the range of 1–3 mM, but preferably at 2 mM), magnesium (at a final concentration of 3–5 mM, but preferably at 4 mM) and manganese (at a final concentration of 1–3 mM, but preferably at 2 mM). Subsequently, the extent to which the DNA binding protein binds with its DNA binding partner is detected, using known methods. The same reagents are combined and processed in the same manner in the absence of the compound being assessed; this serves as a control sample.

In one embodiment, the ability of a compound to inhibit activation of a cellular transduction pathway which is activated by binding of EGF to its cell surface receptor is assessed as follows: a compound being assessed is combined with partially soluble membrane fractions from cells with epidermal growth factor cell surface receptors, preferably cells which are highly enriched in these receptors, such as A431 cells; the cytoplasmic fractions from any cells with a DNA-binding protein whose binding to its binding partner is activated by binding of EGF to receptors on the membrane fractions; epidermal growth factor; ATP; magnesium; manganese; and its DNA-binding partner. The control sample includes the same reagents but lacks the compound being assessed; it is treated in the same manner as the test sample (i.e., the combination of reagents which includes the compound being assessed).

In another embodiment, the ability of a compound to inhibit activation of a cellular transduction pathway which is activated by binding PDGF to its cell surface receptor is assessed as follows: a compound being assessed is combined with a membrane fraction from cells with platelet derived growth factor cell surface receptors, preferably cells which are highly enriched in these receptors; the cytoplasmic fraction from any cells with a DNA-binding protein whose binding to its binding partner is activated by binding of PDGF to receptors on the membrane fraction; platelet derived growth factor; ATP; magnesium; manganese; and its DNA-binding partner. The control sample includes the same reagents, but lacks the compound being assessed.

It is reasonable to expect that growth factors other than EGF and PDGF similarly activate cellular signal transduction pathways. The ability of a compound to inhibit or enhance activation of such pathways can also be assessed by the present method. In each case, the assay is carried out as described above for EGF, except that the cell fractions used will be from cells with the appropriate receptor.

In one embodiment of the present method, the growth factor receptor is activated through the use of a detergent, which partially solubilizes the receptor and replaces the need for growth factor to activate the cell surface receptors. In this embodiment, the combination includes the following: the compound to be assessed for its ability to inhibit the cellular signal transduction pathway; detergent sufficient to partially solubilize the cell surface receptors and activate them in a manner similar to that resulting from binding of the growth factor to the receptor (at a lower concentration than that used to only partially solubilize the membrane fraction); a partially soluble membrane fraction from cells with cell surface growth factor receptors; a cytoplasmic fraction from any cells with a DNA-binding protein whose binding to its binding partner is activated by binding of growth factor to the receptors on the membrane fraction; ATP; magnesium (at a final concentration in the range of 4–6 mM, but preferably at 5 mM); manganese (at a final concentration in the range of 4–6 mM, but preferably at 5 mM); and a DNA-binding partner. The control sample includes the same reagents, but lacks the compound being assessed.

In one embodiment of the present invention, binding of c-sis inducible factor (SIF), a DNA binding protein, to its DNA-binding partner, SIE, is detected as a means of assessing activation of a cellular transduction pathway activated by EGF or PDGF. The binding of SIF to SIE is activated within minutes after addition of certain growth factors to cells containing the receptors for such growth factors. As described in Example 1 and shown in FIG. 1, SIF binding to SIE occurs in response to either PDGF or EGF. As described in Example 1, the mediator of SIF binding by EGF is tyrosine kinase.

As also described in Example 1, Applicants have demonstrated involvement of receptor tyrosine kinase in the activation of SIF since anti-phosphotyrosine antibody inhibits activation of SIF, although SIF protein does not itself appear to be a substrate for a tyrosine kinase. Since signal transduction by receptor kinase involves interaction with proteins containing SH2 domains, more evidence for the involvement of receptor tyrosine kinase for SIF activation was demonstrated from the requirement of phosphotyrosine-SH2 interactions as shown in Example 1. In this embodiment of the present method, SIF binding in cell-free extracts in the presence of ATP is assessed. In this embodiment, the following reagents are combined: a compound being assessed; partially soluble membrane fractions from cells with growth factor cell surface receptors; preferably cells highly enriched in these receptors; the cytoplasmic fractions from any cells with SIF present; growth factor (if the assay is being conducted to identify an inhibitor of the cellular signal tansduction pathway whereas if the assay is being conducted to identify an activator, the growth factor would not be present); ATP; magnesium; manganese; and SIE. The effect of the compound on activation of the cellular signal transduction pathway can be assessed by comparing SIF/SIE binding in the presence of the compound to be assessed and in a control sample, which is a combination of the reagents in the absence of the test compound and has been processed in the same manner as the compound-containing combination (i.e., the test sample) in a similar way as described above.

The method of the present invention is useful for identifying compounds useful for treating proliferative disorders, such as cancer; by inactivating the unrelenting cell growth associated with cancer, enhancing the immune system by stimulating growth of immune response cells; and possibly jump-starting cell growth in cells that normally do not grow or accelerating the growth of certain cells. Compounds identified in this method are also the subject of the present invention.

The present invention is illustrated by the following Examples, which are not intended to be limiting in any way.

EXAMPLES

Figure 1:
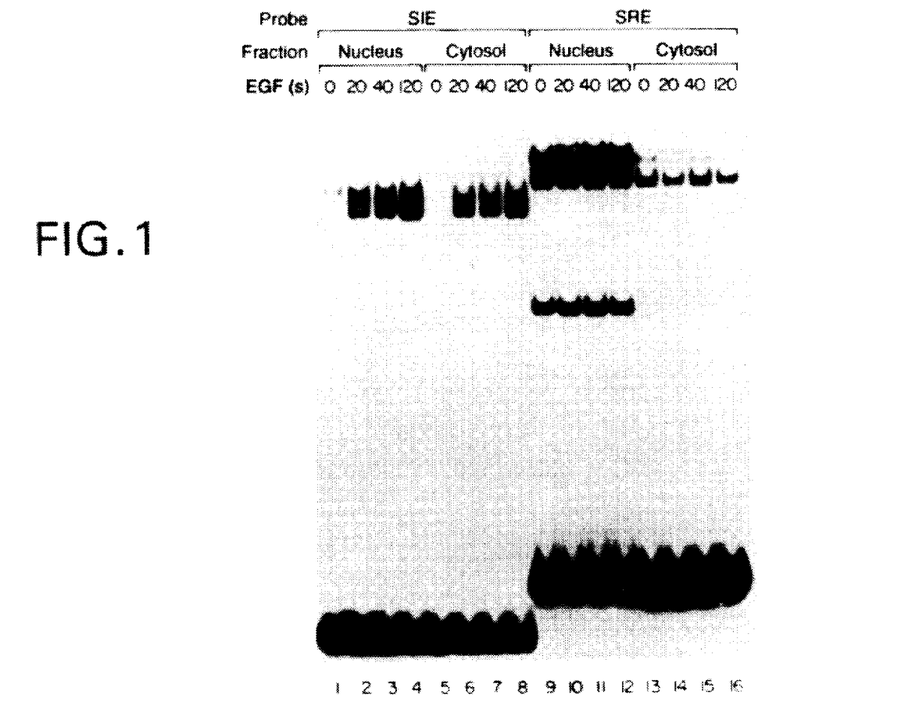
FIG. 1 is a photograph which shows results of the analysis of activation of SIF DNA-binding activity by EGF in A431 cells. The results show the mobility-shift assays of SIE- or SRE-binding proteins performed using cytoplasmic or nuclear fractions prepared from A431 cells treated with EGF for 0, 20, 40, or 120 seconds.

Example 1. Activation by EGF of a DNA-binding protein requires ligand, receptor, ATP, and phosphotyrosine-SH2 interactions Transcription of the c-fos proto-oncogene is rapidly activated by polypeptide growth factors through protein kinase C dependent and independent pathways. Maximal activation requires the serum response element (SRE), located 300 base pairs upstream of the start site. But an additional element, ~25 base pairs 5' of the SRE, has been implicated in c-fos induction by PDGF. This element SIE (c-sis inducible element) binds a protein(s), termed SIF (c-sis inducible factor), whose latent DNA-binding is activated within minutes after treatment of cells with PDGF. Original reports showed that SIF activation in Balb/c 3T3 cells was observed only in response to PDGF, but genomic footprinting experiments suggested that an SIE-binding activity was induced by EGF in the A431 cell line. To determine whether SIF activation occurs in EGF-treated A431 cells, we prepared nuclear and cytoplasmic fractions from these cells and performed mobility-shift analysis with a high-affinity SIF binding site. FIG. 1 shows that SIE binding activity was detectable in both nuclear and cytoplasmic fractions within 20 seconds of treatment with EGF (lanes 1–8). Peak activities were reached within 2 minutes and persisted for at least 60 minutes (data not shown). The activity is sequence-specific (data not shown but see FIG. 2) and comigrated with authentic SIF activity from PDGF-treated Balb/c 3T3 cells. In contrast to SIF, protein binding to the c-fos SRE remained relatively constant following EGF treatment (lanes 9–16). SIF activity was detected at similar levels in nuclear and cytoplasmic extracts (lanes 1–4 vs. 5–8), whereas SRE-binding proteins partitioned nearly completely into the nuclear fraction (lanes 9–12 vs. 13–16), indicating that adequate fractionation had been achieved in this experiment. Thus, the large amount of SIF detected in the cytosolic fraction may be significant.

We performed experiments to identify possible mediators of SIF activation by EGF. Activation of protein kinase C (PKC) by the phorbol ester, PMA, did not induce SIF activity in A431 cells. Furthermore, the induction of SIF by EGF did not require PKC, as it was not affected by PKC down-regulation, nor was it blocked by the PKC inhibitor, staurosporine. Neither calcium, nor cAMP (data not shown) induced SIF activity in these cells, yet both these stimuli as well as PMA, induced c-fos expression (data not shown). Not surprisingly, the tyrosine kinase inhibitor, genistein, completely blocked SIF activation by EGF.

Figure 2:
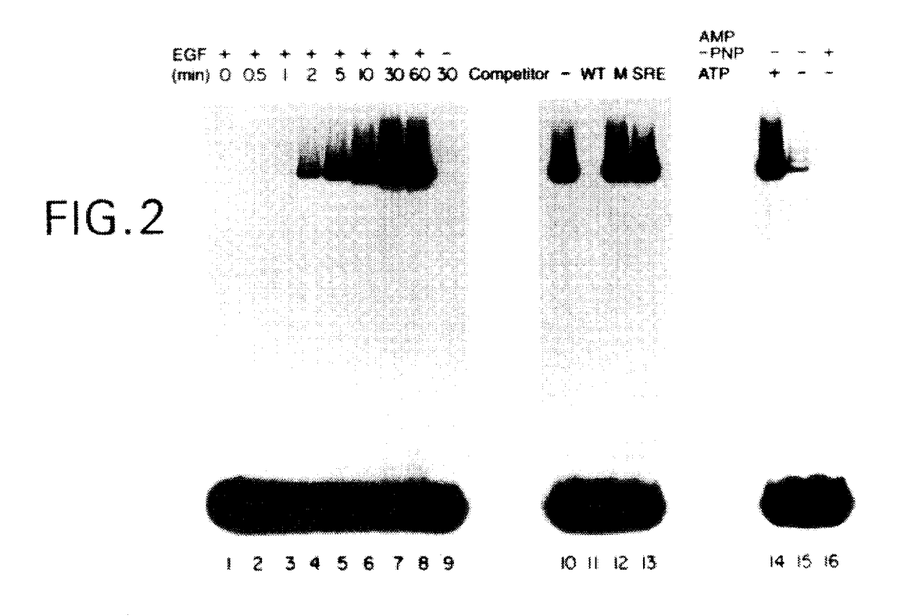
FIG. 2 shows results from cell-free activation of SIF DNA-binding activity by EGF. The results are from SIE mobility-shift assays of cell-free activation reactions.

The level of SIF activity in EGF-treated A431 cells was much higher than we have observed in other cell lines, an observation that may be attributable to the high number of EGF receptors in these cells. Consequently, we investigated whether SIF activation could be observed in cell-free extracts prepared from unstimulated A431 cells. Cells were harvested and fractionated into membrane, cytosol and high-salt nuclear extract fractions. These fractions were mixed and incubated with EGF on ice for 15 minutes. Following EGF pre-treatment, ATP and divalent cations were added and incubation continued for various lengths of time at 30°. After quenching of the reaction, an aliquot was subjected to mobility-shift assay. FIG. 2 shows that SIF activity was generated in these reactions in a time-dependent fashion (lanes 1–8), with peak activity reached at approximately 30 minutes. Activation is very rapid, detectable by as early as 30 seconds on longer exposure of the gel, and not observed in the absence of EGF (lane 9). That this activity is authentic SIF was demonstrated in a competition assay (lanes 10–13). Activity was competed by a high-affinity SIF binding site but not by a biologically inactive mutant nor by the unrelated SRE. Activation of SIF was largely dependent on the addition of ATP. Omission of ATP resulted in a significant reduction of SIF activation (lane 15), and addition of a non-hydrolyzable ATP analogue inhibited activation further (lane 16). We infer that SIF activation requires ATP hydrolysis, consistent with a requirement for, at a minimum, receptor kinase activity.

To determine whether the EGF receptor and other proteins become phosphorylated on tyrosine in the in vitro reaction, we performed anti-phosphotyrosine immunoblots on aliquots of a time course assay similar to that shown in FIG. 2. Reactions left on ice in the presence of EGF contained little phosphotyrosine, but after 30 seconds of incubation, substantial amounts of phosphotyrosine on proteins were detectable. The major phospho- tyrosine-containing protein is the 170 kD EGF receptor, as demonstrated by both immunoprecipitation and immunoblotting with the receptor-specific antibodies (data not shown). Tyrosine phosphorylation of EGF receptors was maximal by 2 minutes and remained high throughout the time course. In reactions incubated for 30 minutes at 30° in the absence of EGF, there was less phosphotyrosine on the receptor and phosphorylation clearly occurs with much slower kinetics. Moreover, in the absence of EGF, tyrosine phosphorylation of other proteins in the reaction was dramatically reduced and several proteins failed to become tyrosine phosphorylasted.

We asked which cellular fractions were required for SIF activation. SIF activation was absolutely dependent on detergent treated A431 membranes. Membranes alone generated low levels of SIF activity in the presence of EGF, but activity was greatly augmented by the inclusion of either cytosol or to a lesser extent nuclear extract. Although not apparent in this experiment, the combination of both cytosol and nuclear extract with membranes only led to an additive induction of SIF activity, suggesting that latent SIF activity and any other activators are present in both fractions. Cytosols from other lines found to contain latent SIF activity could substitute for A431 cytosol, while cytosol from a drosophila embryo cell line that did not contain latent SIF activity was also negative in the in vitro assay. Despite the fact that SIF can be induced by PDGF in Balb/c 3T3 cells and by insulin in HIR 3.5 cells (an NIH 3T3 cell line expressing the human insulin receptor), only detergent treated membranes from A431 cells supported significant SIF formation in vitro (data not shown), suggesting that receptor number may be a critical determinant in the cell-free assay.

These data show that SIF activation is dependent on A431 membranes, which are highly enriched for the EGF receptor, requires ATP, and is accomplished by phosphorylation of the receptor (and other proteins) on tyrosine. To demonstrate that activation was in fact dependent on the EGF receptor, solubilized A431 membranes were incubated with polyclonal antibody against the receptor or with control antibody. Antibody-bound material was removed from the membrane fraction with protein G-agarose beads, and the depleted membrane fractions were used in a SIF activation assay. Membranes mock depleted with control antibody supported EGF-dependent SIF activation, whereas membranes depleted with receptor antibody did not. Thus, EGF receptor is required for SIF activation. When beads containing the EGF-R antibody-bound material were added to A431 cytosol in the activation assay, SIF activation was observed, although at significantly lower levels than mock depleted membranes and in a ligand-independent manner. This activation was not due to non-specific trapping of receptor or activators, as mock-depletion beads did not support any SIF activation. Immunoblotting analysis of aliquots of these reactions with antibodies against the EGF receptor verified the expected presence or absence of receptor (data not shown). Furthermore, immunoblotting analysis with anti-phosphotyrosine antibodies showed significant EGF-dependent tyrosine phosphorylation in the reactions with control supernatanants, whereas reactions with the precipitated receptor had lower levels of ligand-independent tyrosine phosphorylation.

We considered the possibility that SIF, or proteins required for SIF activation might be recruited to the EGF receptor via tyrosine autophosphorylation sites, or that some tyrosine phosphorylated protein might serve as an intermediate in the activation of SIF. To address this question, we added either a monoclonal anti-phosphotyrosine antibody or an irrelevant mouse monoclonal antibody to the activation reaction. Anti-phosphotyrosine antibody specifically inhibited the activation of SIF in a concentration-dependent manner. In contrast, when anti-phosphotyrosine antibody was added after activation but prior to mobility-shift assay, inhibition was not observed. This observation suggests that the anti-phosphotyrosine antibody inhibits activation of SIF rather than directly inhibiting SIF activity itself. These data show that tyrosine phosphorylation is clearly involved in SIF activation in vitro, but suggests that the SIF protein may not itself be a substrate for a tyrosine kinase.

Signal transduction by receptor tyrosine kinases involves interaction with proteins containing SH2 domains. To determine whether phosphotyrosine-SH2 domain interactions were required for SIF activation, we added an *E. coli*-produced SH2 domain as a competitive inhibitor. GST fusion protein containing the SH2 domain from GRB2 inhibited SIF activation in a dose-dependent fashion. Equal amounts of GST protein had no effect. As observed with the anti-phosphotyrosine antibody, the GSTSH2 protein inhibited SIF activation only when added prior to receptor activation, not when added subsequent to activation. These data suggest that protein-protein interactions via phosphotyrosine residues and SH2 domains are required for SIF activation.

We have shown that activation of SIF DNA-binding by EGF in vitro proceeds via a reaction requiring receptor, ATP, and phosphotyrosine-SH2 domain interactions. We do not yet know how many steps are involved in SIF activation. But our data suggest that there is at least one intermediate activity between the receptor tyrosine kinase and SIF protein, because anti-phosphotyrosine antibody blocks activation of SIF without directly affecting SIF that is already active. Thus, our data are in contrast to the recently described activation by α-interferon of ISGF-3, which is activated by direct tyrosine phosphorylation of regulatory subunits. In addition, SIF activation appears to differ from activation of NF-kB, which proceeds by release of an inhibitory subunit, because treatment of cytosolic or nuclear fractions under conditions that release active NF-kB did not lead to SIF activation. The nature of the activating modification of SIF is unknown, but SIF activity is completely extinguished by phosphatase treatment. Together with the lack of reactivity with anti-phosphotyrosine antibodies, these observations suggest that phosphorylation on serine or threonine may be required for SIF activity. Whether such phosphorylation results from the activation of a protein kinase cascade by EGF can be explicitly tested in our in vitro assay.

Example 2. Activation of SIF DNA-Binding Activity by EGF in A431 Cells a) As shown in FIG. 1, mobility-shift assays of SIE (lanes 1–8) or SRE (lanes 9–16) binding proteins were performed using cytoplasmic (lanes 5–8 and 13–16) or nuclear (lanes 1–4 and 9–12) fractions (15 µg protein) prepared from A431 cells treated with EGF (100 ng/ml) for 0 (lanes 1,5,9,13) 20 (lanes 2,6,10,14), 40 (lanes 3,7,11,15) or 120 (lanes 4,8,12, 16) seconds. b) SIE mobility-shift assays of nuclear extracts (10 µg protein) prepared from normal or PKC down-regulated A431 cells that were treated for 10 min with buffer, 100 ng/ml PMA, 100 ng/ml EGF or 1 µM ionomycin. c) SIE mobility-shift assays of nuclear extracts (14 µg protein) prepared from EGF-treated A431 cells subjected to various drug pretreatments. Cells were pretreated for 20 min. with either solvent (DMSO) alone, genistein at 10 ng/ml, 30 ng/ml, 100 ng/ml, or staurosporine at 50 nM, 150 nM and 450 nM, and then incubated for 10 min. in the presence of EGF (100 ng/ml).

Methods

A431 cells (10 cm dishes) were grown to confluence in DMEM with 10% fetal bovine serum (FBS), and then serum-starved for 48 hrs (0.5% FBS). PKC down-regulation A was achieved by treating cells with PMA (500 ng/ml) during the 48 hr serum starvation. a and b) Cells were rinsed twice with PBS, once with PBS containing 1 mM $NA_3VO_4$ and 5 mM NaF (PBS+V+F), and once with hypotonic buffer. All subsequent work was performed on ice or at 4°. Hypotonic buffer with 0.2% NP-40 (0.5 ml) was added directly to the dishes and the cells scraped into microfuge tubes. Lysis was achieved by vigorous mixing, and nuclei were pelleted (16,000 xg for 20 min.). Supernatants were supplemented with NaCl to 120 mM clarified by centrifugation (16,000 xg for 20 min.) after which glycerol was added to 10%. These supernatants are denoted as "cytosolic fractions". The nuclear pellets were resuspended in 150 µl of high salt buffer, the proteins extracted by gentle rocking for 30 min, separated from residual nuclei by centrifugation (16,000 xg for 20 min), and these supernatants denoted "nuclear fractions". Both fractions were frozen in liquid $N_2$ and stored at −70° until use. Protein concentrations were determined by dye binding assay (BioRad) using bovine gamma globulin as a standard. Hypotonic buffer consisted of: 20 mM HEPES (pH 7.9), 20 mM NaF, 1 mM $Na_3VO_4$, 1 mM $Na_4P_2O_7$, 0.125 µM okadaic acid or 0.4 µM microcystin, 1 mM EDTA, 1 mM EGTA, 1 µg/ml each leupeptin, aprotinin and pepstatin, with 1 mM DTT and 0.5 mM PMSF added just before use. This buffer contained 420 mM NaCl and 20% glycerol for nuclear extraction (high salt). For mobility-shift assays, cytoplasmic or nuclear extracts (equal protein) were incubated with poly(dI-dC)poly(dI-dC) in binding buffer for 15 min on ice, after which $^{32}$P-labeled oligonucleotide SIE or SRE probes (20,000 cpm, ~5 fmoles) were added and the reactions (20 µl) incubated for 15 min at 25°. Final binding reactions contained: 13 mM HEPES, pH 7.9, 65 mM NaCl, 1 mM DTT, 0.15 mM EDTA, 8% glycerol, 50 µg/ml poly(dI-dC)poly(dI-dC) and 0–0.02% NP-40 (depending on the fraction). Reactions were analyzed on 5% polyacrylamide gels (39:1 acrylamide:bis) with 2.5% glycerol, in 0.5% TBE buffer. c) NP-40 was not used for cell lysis, although all other reagents were identical. After washing, cells were scraped with PBS+V+F and pelleted. Cells were rinsed with 5 packed-cell volumes (PCV) of hypotonic buffer, pelleted (16,000 xg for 10 sec), resuspended in 3 PCV hypotonic buffer, swollen for 10 min, and lysed by 5 paired passages through a 25 ga. needle. The nuclei were pelleted by centrifugation (16,000 xg for 15 sec) and extracted as above with 2.5 PCV of high salt buffer. Mobility shift assays were performed as described above, except that binding reactions contained 2% Ficoll 400 and 4% glycerol.

Example 3. Cell Free Activation of SIF DNA-Binding by EGF a) As shown in FIG. 2, SIE mobility-shift assays of cell-free activation reactions were performed. Reactions (20 µl) containing membrane, cytoplasmic and nuclear fractions (~20 ug protein of each fraction) prepared from unstimulated A431 cells were incubated for 15 min on ice in the absence (lane 9) or presence of 2 µg/ml EGF (lanes 1–8, and 10–16), after which, kinase buffer (5 µl) was added and the reactions incubated at 30° for 0 (lane 1), 0.5 (lane 2), 1 (lane 3), 2 (lane 4), 5 (lane 5), 10 (lane 6), 30 (lanes 7 and 9–16) and 60 (lane 8) min before quenching on ice with EDTA (12 mM). Activation reactions contained 4 mM Mg and 2 mM Mn with either 2 mM ATP (lanes 1–14), no ATP (lane 15), or 2 mM AMP-PNP, a non-hydrolyzable analogue of ATP (lane 16). After centrifugation, aliquots of the activation reaction (12 µl) were subjected to SIE mobility-shift assays, in the absence (lanes 1–10, and 14–16) or presence of 100-fold molar excess of unlabeled: SIE (lane 11), mutant SIE (m34) (lane 12) or SRE (lane 13) binding site. b) Anti-phosphotyrosine immunoblot of aliquots of the activation reaction time courses performed in the absence or presence of EGF. Scaled-down (one-half) activation reactions were performed as shown in FIG. 2, except that reactions were terminated by the addition of hot SDS sample buffer containing 10 mM EDTA at 0, 0.5, 1, 2, 5, 15 or 30 min, followed by boiling for 5 min.

Methods

Confluent dishes of A431 cells (20×15 cm plates, ~1.5× $10^9$ cells) were rinsed with ice-cold PBS, scraped from the dishes and pelleted. Cytoplasmic and nuclear high-salt extract fractions were prepared essentially as described with the following differences. Hypotonic buffer described in Example 2 (supplemented with 0.4 mM ammonium molybdate) was substituted for buffer A, and the cells lysed in 3 PCV hypotonic buffer with 20 strokes of a type A pestle. Crude nuclei were extracted with the high salt buffer described in Example 2 by gentle rocking and the nuclear extract (~11 ml) was aliquoted and frozen without dialysis. The low speed supernatant was adjusted to ~120 mM NaCl with 1.3 M NaCl in hypotonic buffer and centrifuged for 60 min at 100,000×g. Glycerol was added to the high-speed supernatant to 10% and this cytosolic fraction was aliquoted without dialysis and frozen. The high-speed pellet was resuspended in 2 PCV of hypotonic buffer containing 150 mM NaCl and 8% glycerol, aliquoted, centrifuged (16,000×g for 30 min), and the membrane pellets frozen. For standard activation reactions, membranes (~600 ug protein) were thawed on ice, resuspended in 90 ul MRB, and 80 ul of resuspended membranes were added to 80 ul of MRB with 0.5% Triton X-100. MRB consisted of 20 mM Tris, pH.7.4, 20 mM NaF, 0.1 mM $Na_3VO_4$, 1 mM EDTA, 10% glycerol, 1 ug/ml each of leupeptin, aprotinin and pepstatin, with 1 mM DTT and 0.5 mM PMSF added just before use. Detergent-treated membrane fraction (6 ul/reaction) was added to tubes containing both cytosolic (8 ul) and nuclear (5 ul) fractions (~20 ug protein of each fraction), and the activation reactions performed as described above. Kinase buffers contained 50 mM HEPES, pH 7.4, 20 mM $MgCl_2$, 10 mM $MnCl_2$ and either 10 mM ATP, no ATP or 10 mM AMP-PNP. Mobility-shift binding reactions contained 2% Ficoll 400 and 4% glycerol instead of 8% glycerol. In b, the volumes of all components in the activation reaction were reduced by 50%. Proteins from aliquots of the quenched activation reactions were resolved by SDS-PAGE (8%) gel and then transferred to nitrocellulose in a semi-dry electroblotting apparatus. The membrane was incubated for 1 h at 25° in PBS containing 3% non-fat dry milk, incubated for 2 h in the same buffer containing 1 ug/ml monoclonal antiphosphotyrosine antibody 4G10 (UBI) and 1% normal sheep serum, washed four times with PBS, incubated 1 h at 25° with sheep anti-mouse IgG-HRP (1:2000) in PBS with 0.1% Tween-20 (PBST) and washed extensively with PBST. Immunoreactive bands were visualized with ECL chemiluminescence as suggested by the manufacturer (Amersham).

Example 4. Fraction and receptor dependence of the in vitro activation of SIF DNA-binding by EGF a) SIE mobility-shift assays of activation reactions containing the indicated A431 cell fractions, in the absence or presence of EGF. b) SIE mobility-shift assays of activation reactions containing EGF and detergent-treated A431 membrane fraction, alone or in combination with cytoplasmic fractions from A431 cells (23 ug), HIR 3.5 cells (36 ug), Schneider ($S_2$) cells (51 ug) or Balb/c 3T3 cells (33 ug). c) SIE mobility-shift assays of activation reactions containing A431 cytoplasmic fraction along with one of the following: detergent solubilized A431 membrane fraction mock-depleted with control sheep IgG, detergent solubilized A431 membrane fraction depleted of EGF receptor with anti-EGF receptor IgG, resuspended protein-G agarose beads from the mock-depletion or beads containing immunoprecipitated EGF receptors, in the absence or presence of EGF.

Methods a) Submaximal amounts of cytoplasmic or nuclear fractions were used where activation reactions (30 min at 30°)

and mobility-shift assays were otherwise as described above. b) The A431 fractions used were prepared as in example 3. Balb/c 3T3 cells and HIR 3.5 cells (an NIH mouse 3T3 cell line overexpressing the human insulin receptor) were grown to confluence, serum-starved for 48 h (0.5% CS and FBS respectively), and fractions from 10 plates (15 cm) of each cell line were prepared as described for A431 cells. D. melanogaster Schneider ($S_2$) cells were grown to a density of ~$3 \times 10^6$ cells/ml in Schneiders medium with 10% heat-inactivated FBS. Cells from two flasks ($6.0 \times 10^7$) were collected by centrifugation, washed three times with ice-cold PBS, and fractions prepared as described in example 2. Activation reactions (30 min at 30°) and mobility-shift assays were performed as described in example 3. c) A431 membranes (~600 ug protein) were resuspended in 60 ul MRB containing 130 mM NaCl, and 20 ul of this was added to an equal volume of the same buffer supplemented with 2% Triton X-100. Aliquots (12 ul) of membranes were incubated with equal volumes of normal sheep IgG (2 mg/ml in PBS) or sheep anti-EGFR IgG (2 mg/ml in PBS) (UBI) and both were incubated overnight at 4°. Protein-G agarose (12 ul of a 50:50 slurry in MRB containing 130 mM NaCl and 0.5% Triton X-100) was added to each tube and immune complexes collected by gentle rocking for 2 h at 4°. The beads were pelleted (16,000×15 sec), supernatants removed, and aliquots of each supernatant were assayed in activation reactions with A431 cytoplasmic fraction (+/− EGF). The pellets were washed three times with MRB 130 containing 0.5% Triton X-100, resuspended in the same buffer and aliquots of each were assayed in activation reactions with A431 cytoplasmic fraction (+/− EGF). Activation reactions (30 min at 30°) and mobility-shift assays were performed as described above.

Example 5 In vitro activation of SIF DNA-binding activity requires phosphotyrosine-SH2 domain interactions a) SIE mobility-shift assays of activation reactions where antibodies were added before or after the 30 min incubation at 30° (activation). Reactions were assembled on ice in the absence or presence of EGF. Two reactions received 3 ul PBS both before and after activation, whereas all others received 3 ul PBS either before or after activation. Indicated amounts (1 ug–40 ug/ml) of a monoclonal anti-phosphotyrosine antibody or an irrelevant monoclonal antibody (12 CA5) in 3 ul PBS were added either before or after activation. b) SIE mobility-shift assays of activation reactions performed in the absence or presence of EGF. Either buffer or the indicated amounts (1 ug–40 ug/ml) of control GST protein or GST-SH2 domain fusion protein were added before activation.

Methods

Fractions from unstimulated A431 cells were prepared as described. a) Tubes containing a mix of cytoplasmic (5 ul), nuclear (3 ul) and detergent-treated membrane (6 ul) fractions received either 3 ul PBS or 3 ul PBS containing the indicated amount of specific antibody (antibody pre-activation). Antibody was either the antiphosphotyrosine mouse monoclonal, 4G10 (UBI), or the anti-HA epitope mouse monoclonal, 12C5. Either water or EGF was added, reactions incubated on ice for 15 min, and activation performed as described above (30 min at 30°). After quenching on ice with EDTA, reactions received either 3 ul PBS or 3 ul PBS containing antibody (antibody post-activation), and aliquots (13 ul) were subjected to SIE mobility-shift assay. Detergent-treated membrane fraction (3 ul) was added to tubes containing a mix of cytoplasmic fraction (5 ul), cytoplasmic buffer (1 ul) and nuclear fraction (4 ul). To these, either 3 ul PBS, or 3 ul PBS containing the indicated amounts of either

*E. coli* produced GST protein or *E. coli* produced GRB2 protein was added. Water or EGF (2 ug/ml) was added, reactions incubated on ice for 15 min, and activation performed as described above (30 min ay 30°). Aliquots (12 ul) were subjected to SIE mobility-shift assay as above. Control experiments (data not shown), demonstrated that neither the GST of SH2-GST fusion protein inhibited SIF DNA-binding when added after activation. The GST protein and GRB2 $SH2_{(50-161)}$-GST fusion protein were prepared as described.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of assessing the ability of a compound to inhibit activation of a cellular signal transduction pathway, comprising the steps of:
   a) combining:
      1) a compound to be assessed;
      2) a partially soluble membrane fraction from A431 cells which have cell surface growth factor receptors with intrinsic tyrosine kinase activities;
      3) a cytoplasmic fraction from cells, wherein the cytoplasmic fraction contains c-sis inducible factor whose binding to its binding partner is activated by activation of the tyrosine kinase activities of the cell surface growth factor receptors in the membrane fraction of (a)(2);
      4) c-sis inducible element;
      5) adenosine triphosphate;
      6) magnesium;
      7) manganese; and
      8) an agent which activates the tyrosine kinase activities of the cell surface growth factor receptors;
   b) maintaining the combination produced in (a) under conditions appropriate for activation of the tyrosine kinase activities of the cell surface growth factor receptors and binding of the c-sis inducible factor of (a)(3) with the c-sis inducible element of (a)(4);
   c) determining the extent to which binding of the c-sis inducible factor to c-sis inducible element occurs in the presence of the compound to be assessed; and
   d) comparing the extent of binding in (c) with the extent to which binding occurs in the absence of the compound,
   wherein binding to a lesser extent in the presence of the compound than in its absence is indicative of the ability of the compound to inhibit activation of a cellular signal transduction pathway.

2. A method of claim 1, wherein the cell surface growth factor receptor of (a)(2) is platelet derived growth factor receptor and the agent of (a)(8) is selected from the group consisting of: detergent and platelet derived growth factor.

3. A method of claim 1, wherein the cell surface growth factor receptor of (a)(2) is epidermal growth factor receptor and the agent of (a)(8) is selected from the group consisting of: detergent and epidermal growth factor.

4. A method of assessing the ability of a compound to activate a cellular signal transduction pathway which is activated by binding of a growth factor to a cell surface growth factor receptor, comprising the steps of:
   a) combining:
      1) a compound to be assessed;

2) a partially soluble membrane fraction from A431 cells which have cell surface growth factor receptors with intrinsic tyrosine kinase activities;
3) a cytoplasmic fraction from cells, wherein the cytoplasmic fraction contains c-sis inducible factor whose binding to its binding partner is activated by binding of the growth factor to cell surface growth factor receptors in the membrane fraction of (a)(2);
4) c-sis inducible element;
5) adenosine triphosphate (ATP);
6) magnesium;
7) manganese; and b) maintaining the combination produced in (a) under conditions appropriate for activation of the tyrosine kinase activities of the cell surface growth factor receptors in the membrane fraction of (a)(2) and binding of the c-sis inducible factor of (a)(3) with the c-sis inducible element of (a)(4);

c) determining the extent to which binding of the c-sis inducible factor to c-sis inducible element occurs in the presence of the compound being assessed; and d) comparing the extent of binding determined in (c) with the extent to which binding occurs in the absence of the compound, wherein binding to a greater extent in the presence of the compound than in its absence is indicative of the ability of the compound to activate a cellular signal transduction pathway.

5. A method of claim 4, wherein the cell surface growth factor receptor of (a)(2) is selected from the group consisting of: platelet derived growth factor receptor and epidermal growth factor receptor.

* * * * *